United States Patent [19]

Freed

[11] 4,339,579

[45] Jul. 13, 1982

[54] 2,6-BIS-(PYRROLOPYRAZINYL)PYRAZINES

[75] Inventor: Meier E. Freed, Paoli, Pa.

[73] Assignee: American Home Products Corporation, New York, N.Y.

[21] Appl. No.: 221,124

[22] Filed: Dec. 29, 1980

[51] Int. Cl.$^3$ ............................................ C07D 487/04
[52] U.S. Cl. .................................... 544/349; 424/250
[58] Field of Search ........................................ 544/349

[56] References Cited

U.S. PATENT DOCUMENTS

| | | | |
|---|---|---|---|
| 3,294,638 | 12/1966 | Lutz | 544/336 |
| 3,388,128 | 6/1968 | Day et al. | 544/349 |
| 4,188,389 | 2/1980 | Jirkovsky | 544/349 |
| 4,230,856 | 10/1980 | Skoldinov et al. | 544/349 |

FOREIGN PATENT DOCUMENTS 1492528 11/1977 United Kingdom .

OTHER PUBLICATIONS

Freed et al., Journal of Organic Chemistry, vol. 25, pp. 2108–2113 (1960).

*Primary Examiner*—Donald G. Daus
*Assistant Examiner*—Sharon A. Gibson
*Attorney, Agent, or Firm*—George Tarnowski

[57] ABSTRACT

There are disclosed 2,6-bis-(pyrrolopyrazinyl)pyrazines which exhibit antihypertensive activity.

2 Claims, No Drawings

2,6-BIS-(PYRROLOPYRAZINYL)PYRAZINES

The invention comprises 2,6-disubstituted pyrazinyl derivatives where the 6- or 2,6-substituent is a diazabicycloalkane. The compounds of the invention exhibit anti-hypertensive effects when administered to hypertensive animals and also exhibit anti-secretory properties.

The compounds of the invention have the general formula:

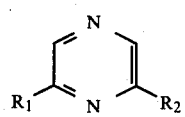

wherein $R_1$ is hydrogen, halo, lower alkoxy of 1–4 carbon atoms, diloweralkylaminoloweralkoxy in which each alkyl moiety contains 1–4 carbon atoms or

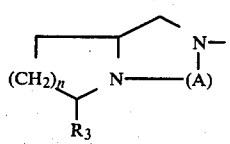

wherein $R_3$ is hydrogen, loweralkyl of 1–4 carbon atoms, phenyl or phenyl substituted with halo, lower alkyl of 1–4 carbon atoms or lower alkoxy of 1–4 carbon atoms;

A is

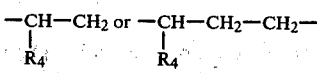

where $R_4$ is hydrogen, lower alkyl of 1–4 carbon atoms or phenyl; and
n is 1–3;
$R_2$ is

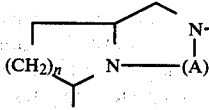

wherein $R_3$ is hydrogen, lower alkyl of 1–4 carbon atoms, phenyl or phenyl substituted with halo, lower alkyl of 1–4 carbon atoms or lower alkoxyl of 1–4 carbon atoms;

A is

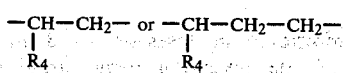

where $R_4$ is hydrogen, lower alkoxy of 1-4 carbon atoms or phenyl;
n is 1-3; or
a pharmaceutically acceptable salt thereof.

The term halo, as used herein, refers to chloro, fluoro, and bromo.

The compounds of the invention may be prepared by a variety of synthetic routes. According to one route, 2,6-dichloropyrazine is reacted with an appropriate diazabicycloalkane and triethylamine in an organic solvent, such as acetonitrile for example:

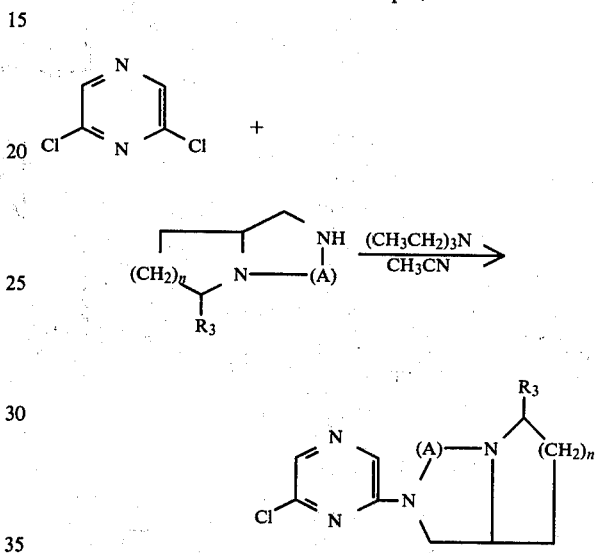

where $R_3$, A and n are as described hereinbefore.

Once the 6-substituent is prepared, the 2-chloro substituent on the pyrazine ring can be reacted to prepare other 2-position substituents. In this case, appropriate solvents and reaction conditions are necessary to replace the 2-chloro group.

Another route of preparation is the following:

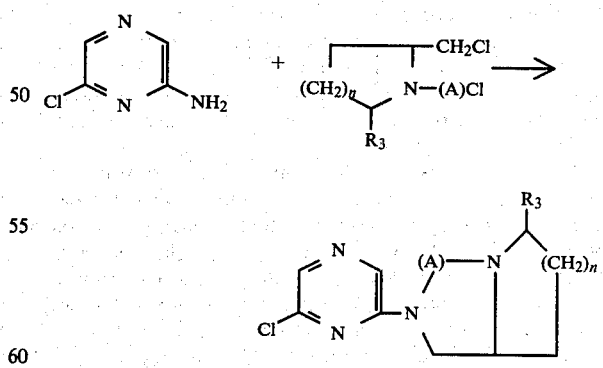

where $R_3$, A and n are as described hereinbefore. In this case, the starting 2-chloro-6-amino-pyrazine can be prepared from 2,6-dichloropyrazine by conventional techniques.

A further synthetic method of preparation is as follows:

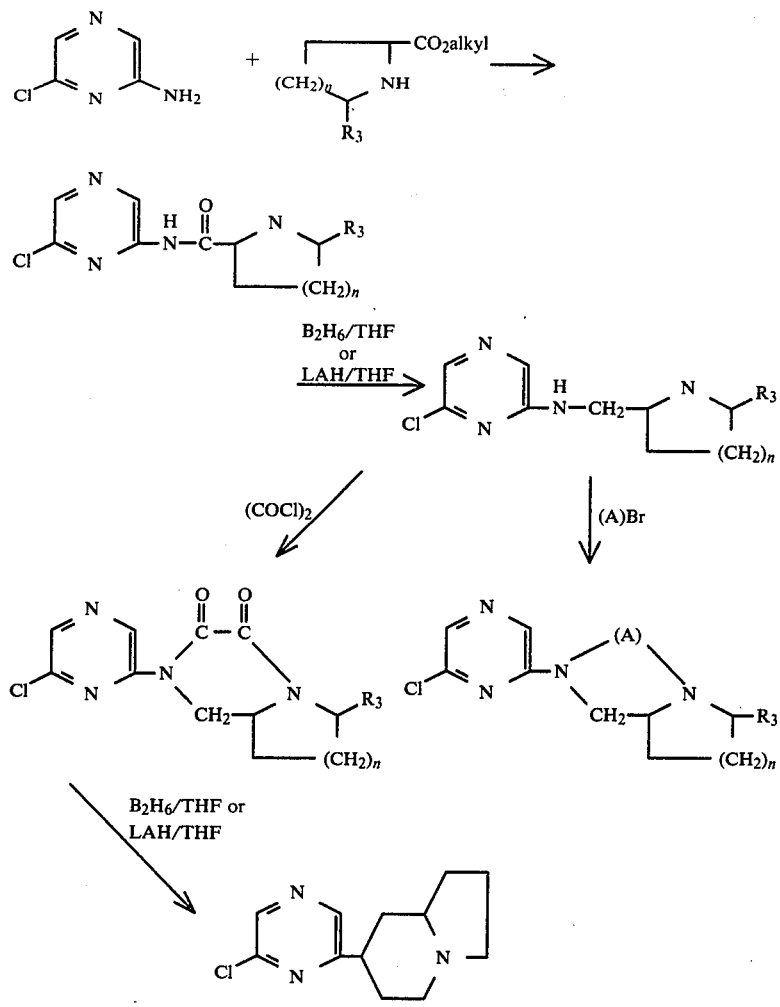

The starting material 1,4-diazabicycloalkanes used in the first described route of preparation can be prepared according to the method disclosed in Freed et al, *J. Org. Chem.* 25, 2108–2113 (1960).

Of course, other methods of preparation, which will occur to those skilled in the art, may also be employed to prepare the compounds of the invention.

Since the compounds of the invention can possess an asymmetric carbon atom, optical enantiomorphs are possible, and the compounds of the invention may be in the form of the pure enantiomorph or mixtures thereof, such as the racemates.

The compounds may be obtained in the form of the pure enantiomorph either by resolving a desired racemic product or by resolving a racemic starting material or intermediate at any convenient stage of the synthesis. Methods of carrying out the resolution are well-known in the art of chemistry. For example, the desired racemate may be treated with an optically active carboxylic acid and the optically active addition salts may be separated by standard techniques.

The compounds of the invention may exist either in the form of the free base or the pharmaceutically acceptable salt. Methods for converting one such form to another will be obvious to one skilled in the art of chemistry.

For pharmacological use, the compounds may be administered in the form of a pharmaceutically acceptable salt of a non-toxic inorganic acid. The salts may be prepared by methods well-known in the art. Appropriate salts are those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. Such salts are included in the scope of the invention.

The compounds of the invention are effective in lowering blood pressures as shown in standard tests using hypertensive rats. Such tests are conducted on spontaneously or surgically hypertensive rats. Test groups and control groups usually consist of 4–6 rats, and the test compounds and reference compounds are administered either orally or intraperitoneally. Systolic blood pressures are measured by an indirect technique using the Decker Caudal Plethysmograph or other appropriate sensor, and readings are taken prior to drug administration and periodically thereafter, for example at 1.5, 4, and 24 hours after administration. Results are analyzed statistically. Reference compounds used include clonidine, hydralazine, guanethidine, methyldopa, and reserpine.

When administered in doses of 10–75 mg/kg., the compounds of the invention demonstrate slight to marked abilities to reduce blood pressures. The antihypertensive activity of a compound is rated as follows:

| Activity | Systolic Decrease In Blood Pressure |
|---|---|
| Not Significant (NS) | <15 mm. Hg. |
| Borderline (BDL) | 15–25 |
| Slight (SLT) | 25–35 |
| Moderate (MOD) | 25–50 |
| Marked (MKD) | over 50 |

When tested in spontaneously hypertensive rats as described above, compounds of the invention gave the following results:

| Compound | Dose (mg/kg) | Activity |
|---|---|---|
| 2-(6-chloro-2-pyrazinyl)-octahydro-2H-pyrido[1,2-a]pyrazine | 75 | MKD |
|  | 50 | MKD |
|  | 25 | MOD |
|  | 10 | SLT |
| 2-(6-chloro-2-pyrazinyl)-octahydro-pyrrolo[1,2-a]pyrazine | 50 | MOD |

A number of standard pharmacological tests may also be employed to demonstrate the effectiveness of the compounds of the invention in inhibiting gastric secretions. Such antisecretory activity is also evidence of anti-ulcer activity. One such test is a modification of the method of Shay et al., *Gastroenterology*, 26, 906–913 (1954). In this procedure male Charles River rats weighing 200–300 grams are deprived of food but not water for 24 hours prior to use. Water is, however, withheld during the experiment. The rats are weighed, anesthetized with ether and the pylorus ligated according to the method of Shay, et al. Treatment or vehicle control is then administered interduodenally (i.d.) or subcutaneously (s.c.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food, or hemolysis are eliminated. An aliquot of each is frozen for later analysis of $Na^+$, $K^+$, and $Cl^-$ concentration. The pH is measured and 1 ml. of gastric juice is titrated with 0.1 NaOH to a pH of 7.0–7.4. The data are analyzed for either a Student's t-test or an analysis of variance depending upon which test is appropriate.

At a dose of 32 mg/kg 2-(6-chloro-2-pyrazinyl)-octahydro-2H-pyrido[1,2-a]pyrazine exhibited a 45 percent inhibition of secretion in the modified Shay et al procedure.

When employed to lower blood pressures or to reduce gastric secretions, the effective dosage of the substance active for such treatment will vary according to the particular compound being employed, the severity and nature of condition being treated. Therapy should be initiated at lower doses (in mg/kg/day) in the effective ranges given above for the prescribed activity, the dosage thereafter being increased, if necessary, to produce the desired anti-hypertensive or anti-secretory effect.

Further, when employed as anti-ulcer, anti-secretoy, or anti-hypertensive agents, the compounds of the invention, or pharmacologically acceptable acid addition salts thereof, may be administered alone or in combination with pharmaceutically acceptable carriers. The proportion and nature of such carriers would be determined by the solubility and other chemical properties of the compound selected, the chosen route of administration, and standard pharmaceutical practice.

The following examples further illustrate the best mode of practicing this invention.

EXAMPLE 1

2-(6-Chloro-2-pyrazinyl)-octahydro-2H-pyrido[1,2-a]pyrazine

A solution of octahydro-2H-pyrido[1,2-a]pyrazine (4 gm, 0.029 moles), 2,6-dichloropyrazine (4.28 gm, 0.029 moles) and triethylamine (8 ml. 0.06 moles) in 75 ml of acetonitrile is heated under reflux for 4 hours. After cooling, the precipitate is filtered off and washed with a little acetonitrile. The filtrate is concentrated under reduced pressure and the resulting residue is partitioned between water and ether. The aqueous layer is made basic with potassium carbonate and extracted 3 times with 100 ml. portions of ether. The combined ether layer is washed with saline and dried over sodium sulfate. After filtering off the drying agent the clear filtrate is made acidic with dry hydrogen chloride gas. The precipitate is filtered off, washed with ether and dried. After two crystallizations from ethanol there is obtained a 4.5 gm (54 percent) yield of title compound, m.p. 298°–301° C.

EXAMPLE 2

(1)-2-(6-Chloro-2-pyrazine)-octahydro-pyrrolo[1,2-a]pyrazine

In the manner of preparation described in Example 1, 2,6-dichloropyrazine and 1-octahydro pyrrolo-[1,2-a]pyrazine (in equal molar quantities) are refluxed in acetonitrile in the presence of triethylamine. There is obtained 2.5 gm. (56 percent) of title compound, m.p. 294°–295° C. $[\alpha]_D^{28} \times -12.95$ (1% methanol)

EXAMPLE 3

(1) 2-(6-Ethoxy-2-pyrazinyl)-octahydropyrrolo[1,2-a]pyrazine

To a solution of sodium ethoxide, prepared by the cautious addition of sodium hydride (50 percent in oil), 2.4 gms. (0.05 mole), to 25 ml absolute ethanol is added 1.5 gms. (0.00545 mole) of (1) 2-(6-chloro-2-pyrazinyl)-octahydro-2H-pyrrolo [1,2-a]pyrazine dihydrochloride. The solution is stirred and heated at reflux for 4 hours. Xylene, 50 ml., is then added slowly while distilling off ethanol. When the solution temperature reaches 130° distillation is halted and refluxing continued for 18 hours. The reaction is cooled and the xylene solution is washed with saline. After drying overnight (sodium sulfate), the solvent is removed under vacuum leaving a yellow oil. This is crystallized from pentane. There is obtained 0.7 gms., of title compound m.p. 101°–102° C.

Analysis For: $C_{13}H_{20}N_4$: Calculated: C, 62.87; H, 8.12; N, 22.57; Found: C, 62.11; H, 8.05; N, 22.45.

The hydrochloride salt is prepared in methanol and crystallized from methanol-acetone, m.p. 204°–6° C.

EXAMPLE 4

(1)

2,6-bis-(octahydro-2H-pyrrolo[1,2-a]pyrazinyl)pyrazine

To a solution of 1-2-(6-chloro-2-pyrazinyl)-octahydro-2H-pyrrolo[1,2-a]pyrazine-1.5 gms. (0.00545 mole), in 50 ml. of seive dried dimethyl sulfoxide is added first triethylamine (1.4 ml., 0.01 mole), then 1.8 gms. (0.014 mole) 1-octahydro-2H-pyrrolo[1,2-a]pyrazine. Stirred and heated at 50°–60° for 18 hours and then cooled. The solvent is removed under vacuum. The residue is then partitioned between methylene dichloride and water. The ersanic layer is washed with saline, dried, and concentrated to a dark oil which solidifies on standing. The solid is dissolved in ethanol and acidified by dropwise addition of a solution of dry hydrogen chloride in absolute ethanol. Crystallization yields 0.8 gms. of title compound as the hydrochloride salt, m.p. 285°–6° C.

EXAMPLE 5

2-(6-Chloro-2-pyrazine)-octahydro-6-phenylpyrrolo[1,2-a]pyrazine

In the manner of preparation described in Example 1, 8-phenyl-1,4-diazabicyclo[4.3.0]nonane and 2,6-dichloropyrazine (in equal molar quantities) are refluxed together in acetonitrile containing an excess of triethylamine. On work-up the title compound is obtained.

What is claimed is:

1. A compound of the formula:

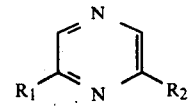

wherein $R_1$ and $R_2$ are

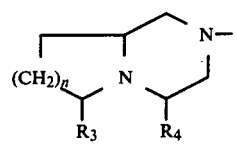

wherein $R_3$ is hydrogen, lower alkyl of 1–4 carbon atoms, phenyl or phenyl mono substituted with halo, lower alkyl of 1–4 carbon atoms or lower alkoxy of 1–4 carbon atoms;

$R_4$ is hydrogen, lower alkyl of 1–4 carbon atoms or phenyl; and n is 1–3; or a pharmaceutically acceptable salt thereof.

2. The compound of claim 1, which is 2,6-bis-(octahydro-2H-pyrrolo[1,2-a]pyrazinyl)pyrazine.

* * * * *